United States Patent [19]

Caimi

[11] Patent Number: 4,893,894
[45] Date of Patent: Jan. 16, 1990

[54] EVANESCENT SENSOR

[75] Inventor: Frank M. Caimi, Vero Beach, Fla.

[73] Assignee: Mine Safety Appliances Company, Pittsburgh, Pa.

[21] Appl. No.: 187,860

[22] Filed: Apr. 29, 1988

[51] Int. Cl.$^4$ ............................ G02B 6/02; G02B 6/16
[52] U.S. Cl. ................................ 350/96.29; 350/96.33
[58] Field of Search ........................... 350/96.29, 96.33

[56] References Cited

U.S. PATENT DOCUMENTS

| 4,678,328 | 7/1987 | Craig et al. | 350/96.29 |
| 4,693,553 | 9/1987 | Sasaki et al. | 350/96.29 |

FOREIGN PATENT DOCUMENTS

WO83/01112 3/1983 PCT Int'l Appl. .

Primary Examiner—William L. Sikes
Assistant Examiner—Robert E. Wise
Attorney, Agent, or Firm—Reed Smith Shaw & McClay

[57] ABSTRACT

The present invention pertains to a sensor for detecting species concentrations in an analyte. The sensor includes an optical fiber. The optical fiber has a core and an intermediate dielectric layer circumferentially surrounding the core. The core has an index of refraction which is greater than the index of refraction of the intermediate dielectric layer. The intermediate dielectric layer has an index of refraction which is greater than the index of refraction of the analyte. The intermediate dielectric layer is of a thickness such that there is a minimal decay of an evanescent wave passing through the intermediate dielectric layer. Moreover, the intermediate dielectric layer is also unreactive to light. The sensor also includes a modal selector disposed to launch light into the core of the optical fiber into a desired mode or modes.

11 Claims, 1 Drawing Sheet

EVANESCENT SENSOR

FIELD OF THE INVENTION

The present invention is related to evanescent sensors. More specifically, the present invention is related to an evanescent sensor which has an optical fiber comprised of a core and an intermediate dielectric layer, with the intermediate dielectric layer disposed between the core and an analyte.

BACKGROUND OF THE INVENTION

Evanescent sensors comprised of a single layer optical fiber are well known. See, U.S. Pat. No. 4,608,344 by Carter, et al., and P. H. Paul and G. Kychakoff, "Fiber-Optic Evanescent Field Absorption Sensor", Appl. Phys. Lett. 51(1), July, 1987. An advantage of evanescent sensors is their inherent immunity from scattering effects in the analyte on light transmission, unlike conventional transmission type spectrometers.

A problem that commonly exists with such sensors is the ability to maintain the desired modal structure of the light propagating through the optical fiber. Additional problems are encountered with crack propagation into the waveguiding region, causing deterioration of the sensors characteristic. With time and contact with certain analyte materials. An example of hydrogen penetration in cables used underwater is given by R. Adams, *Lightwave,* May 1986, p. 37. Near a critical angle (defined by Snell's law) at the interface of a liquid or solid, otherwise known as the analyte, and the fiber, the index of refraction of the analyte is sensitive to external conditions such as temperature, dilution, pressure, etc. As the index of refraction of the analyte changes, the critical angle also changes. Since the evanescent sensor is most sensitive at or very near the critical angle, as the critical angle changes with the modal structure constant, the sensitivity of the sensor decreases. Also, some of the light which otherwise would propagate through the fiber, instead escapes from the fiber.

SUMMARY OF THE INVENTION

The present invention pertains to a sensor for detecting species concentrations in an analyte. The sensor is comprised of an optical fiber. The optical fiber has a core and an intermediate dielectric layer circumferentially surrounding the core. The core has an index of refraction which is greater than the index of refraction of the intermediate dielectric layer. The intermediate dielectric layer has an index of refraction which is greater than the index of refraction of the analyte. The intermediate dielectric layer is of a thickness such that there is a minimal decay of an evanescent wave passing through the intermediate dielectric layer The opposite condition is preferred for construction of communication fibers. Moreover, the intermediate dielectric layer is also unreactive to light. The sensor also includes a modal selector disposed to launch light into the core of the optical fiber into a desired mode or modes.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
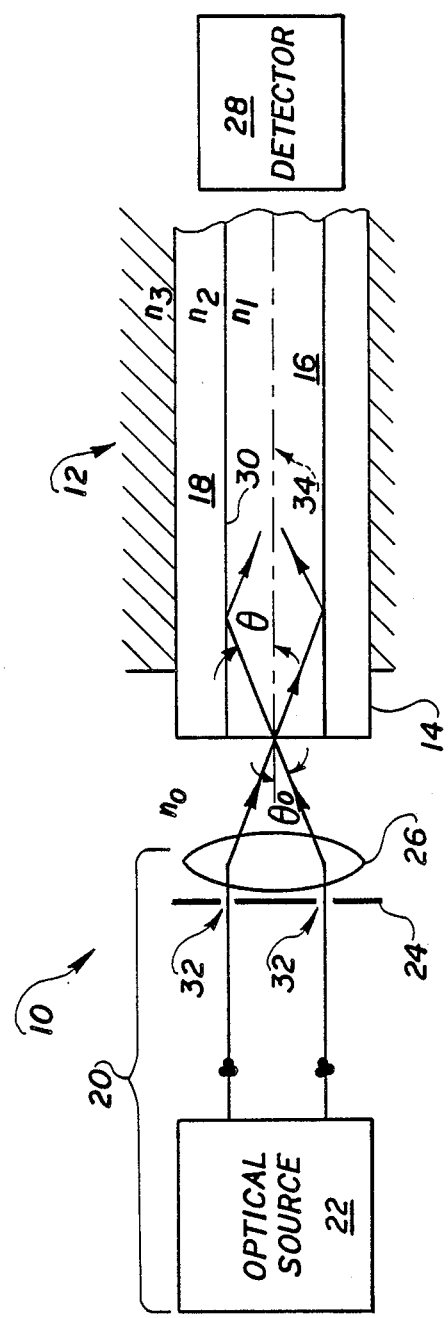
FIG. 1 is a schematic diagram of a fiber optic based spectrometer system.

Referring now to the drawings and more particularly to FIG. 1 thereof, there is shown a sensor 10 for detecting species concentrations in an analyte 12. The sensor 10 is comprised of a cylindrical dielectric waveguide or an optical fiber 14. The optical fiber 14 has a core 16 and an intermediate dielectric layer 18 circumferentially surrounding the core 16. The core 16 has an index of refraction greater than the index of refraction of the intermediate dielectric layer 18. The intermediate dielectric layer 18 has an index of refraction greater than the index of refraction of the analyte 12. The intermediate dielectric layer 18 is of a thickness such that there is a minimal decay of an evanescent wave passing through the intermediate dielectric layer 18. The intermediate dielectric layer 18 is also unreactive to light.

The sensor 10 is additionally comprised of a modal selector 20. The modal selector 20 can include an optical source 22 disposed to provide light to the core 16 of the optical fiber 14. The modal selector 20 can also include an aperture mask 24 disposed between the core 16 of the optical fiber 14 and the optical source 22. The aperture mask 24 determines the mode at which the light from the optical source 22 is launched into the core 16 of the optical fiber 14. Additionally, a lens 26 is disposed between the aperture mask 24 and the core 16 of the optical fiber 14. The lens 26 focuses light passing through the aperture mask 24 into the core 16 of the optical fiber 14 as is well known in the art. Moreover, the modal selector 20 can include a detector 28 disposed to receive light emitted from the core 16 of the optical fiber 14.

Preferably, the optical source 22 is a collimated light source such as a laser. Other optical sources 22 can include luminescent or superluminescent diodes or thermal sources. The optical source 22 may be modulated at low frequency so that techniques of synchronous detection that are well known in the art may be used to reject random noise from external lighting and to reduce random distributions due to temperature, pressure, flexure, etc.

The optical fiber assembly 14 can be configured as, but not limited to, a step index, a graded index, a single mode, or a polarization preserving type. The material used for construction of the optical fiber 14 is selected for the wavelength of use and for compatibility with the analyte. A water resistant coating may be used as the intermediate dielectric layer or as an additional layer 18 over a more conventional intermediate dielectric layer.

The fiber core 16 can range in size from two microns to four millimeters in diameter. The core 16 materials chosen for operation in the visible region of the spectrum might preferably be silica; however, a great variety of other materials are possible, particularly in the infrared range. Chalcogenide glasses, metal, halides, and various metal-oxides, sulfides or selenides all have utility as dielectric transmission media in the infrared range. Such materials can exhibit indices of refraction from 1.3 for some alkali halides to as high as 4 for certain semiconductors. Typically, however, the index of refraction of the core material is between 1.4 and 1.6. The intermediate dielectric layer 18 is preferably selected to be of smaller refractive index than the core 6 at the wavelength of operation by some fraction $$\Delta = \frac{n_{core} - n_{inter}}{n_{core}}$$

This fraction is preferably much less than 1 (usually <1%) and determines the critical angle within the fiber. A large fraction implies a small critical angle and therefore a large number of allowed modes which can mix and lessen the sensitivity of the method.

A coating may be used as an intermediate dielectric layer 18 and is typically less than or several times greater in thickness than the wavelength of light of the propagating beam. The Spectran Corporation Hydroshield ™ coating may be used directly as the intermediate dielectric layer 18 in a nominal thickness of 0.025 microns to prevent hydrogen intrusion in aqueous or other environments. It may also be desirable to use additional coatings such as Nylon, Acrylate, Teflon, silicone, etc., as the intermediate dielectric layer 18. In general, the selection of a preferred coating depends upon the application.

Sensitivity is dependent upon the thickness of the intermediate dielectric layer in relation to the core diameter, because of the exponential decay of the field strength in the former. Typically, the intermediate dielectric layer is between 0.01 and 25 microns. An optimal condition is to allow a substantial reduction of the evanescent field, if a variation of the real part of the refractive index in the analyte is expected. In this manner, the allowed modal structure of the core region can be maintained; however, typically at the expense of some sensitivity. For optimum sensitivity, the intermediate dielectric layer 18 thickness is made as small as is practical while maintaining coating integrity, mechanically and chemically. (This is a contrary design philosophy to that of making communication fibers). In the former case, the intermediate dielectric layer 18 thickness may be calculated for a given mode propagating at angle $\theta$ and for a reduction of the evanescent wave fiber intensity by a certain fraction, perhaps 10%. Typical thicknesses are several microns for fibers operated in the visible to near infrared range of the intermediate dielectric layer 18 and with core diameters of several tens of microns.

In the operation of the invention, the mode structure of the light propagating through the core 16 is chosen at or as near as possible to the critical angle $\phi$ as determined by Snell's law, with respect to the interface 30 of the core 16 and intermediate dielectric layer 18. The specific desired modal structure is achieved by altering the placement of the aperture mask 24 which has open or transparent areas 32. By altering the placement of the open or transparent areas 32 of the aperture mask 24, the location the light passing therethrough strikes the lens 26 is controlled. The lens 26 focuses the light it receives into the core 16 of the optical fiber 14, as is well known in the art. Cladding-mode strippers which are also well known in the art may be used to eliminate energy which may be launched into the cladding.

The governing formula for determining the angle $\theta$ of the mode structure of the light propagating through the optical fiber 14 is $$\tan 0 = r/f, = \tan \{Sin^{-1}(Ni/No\sin \theta)\}$$

where r is the radial distance of the open area 32 of the aperture mask 24 from the meridonal axis 34 of the optical fiber 14, f is the focal length of the lens 26, and $\eta$, and $\eta_o$ are the refractive indices of the core and regions outside the fiber, respectively.

Light launched into the core 16 of the optical fiber 14 propagates therethrough experiencing internal reflection. At each reflection point at the core 16-intermediate dielectric layer 18 interface 30 a fractional amount of the light is reflected back into the core 16. As required by the boundary conditions for solution of Maxwell's equations, an evanescent wave of the light proceeds through the interface 30 into the intermediate dielectric layer 18. The distance the evanescent wave travels is a function of the angle at which the light strikes the interface 30 and the polarization of the light. The closer to the critical angle the light strikes the interface 30, the further the evanescent wave penetrates into the intermediate dielectric layer 18. The intermediate dielectric layer 18, being fixed and integral to the core 16, essentially allows the critical angle to remain the same and insulates the core 16 from external conditions that would otherwise change the critical angle. The thickness of the intermediate dielectric layer 18 is such that at least some portion of the evanescent wave propagates through the intermediate dielectric layer 18 to the analyte 12.

The analyte 12, within which the optical fiber 14 is immersed, forms another layer around the core 16. The analyte 12 imposes a boundary condition on the core intermediate dielectric layer 18 interface 30. With the aid of the Maxwell equations, the effects that the intermediate dielectric layer 18 and analyte 12 have on the light in the core 16 can be more specifically identified.

The evanescent wave passes from the intermediate dielectric layer 18 into the analyte 12. The analyte 12 may have one or more contaminants that are sought to be detected or may be the analyte itself. The contaminant, if present in the analyte 12, absorbs energy from the evanescent wave in proportion to the contaminant concentration in the analyte 12. A given contaminant can be detected by using light in the fiber that has a wavelength at which only a given contaminant absorbs the light. The amount of absorption of the evanescent field in the analyte 12 results in a corresponding decrease to the electric field at the intermediate dielectric layer 18-analyte 12 interface. This change in the electric field at the interface causes a corresponding change in the electric field at the core 16-intermediate dielectric layer 18 interface 30. This in turn results in a corresponding reduction of the electric field for the light reflected back into the core 16. As the light propagates through the core 16 by internal reflection, a loss to the light amplitude occurs at each reflection point. When the light is emitted from the optical fiber 14 and received by the detector 28, the amount of the contaminant present in the analyte 12 can be determined by an absolute method or by a differencing method. In the differencing method, the excess loss in the optical fiber 14 exposed to an unknown analyte 12 is compared to the loss exhibited by a reference fiber surrounded by a known analyte.

Alternatively, the wavelength of the optical source 22 may also be scanned or switched by mechanical, electrical, optical or other means to detect the different contaminants in the analyte 12.

Sensitivity of the sensor may be increased by reduction of the intermediate dielectric layer 18 thickness or may be controlled to reduce sensitivity for highly absorbing analytes by increasing the thickness of the intermediate dielectric layer 18. In general, the smaller the intermediate dielectric layer 18 thickness, the greater the excess loss for a given length. The length of the sensor also affects the sensitivity by virtue of increasing the number of reflection points, thereby compounding the loss due to the analyte. The measured output signal being comprised of other signals due, in part, to mode mixing or conversion, intrinsic absorption, or scattered light in the core, in addition to the desired signal, imposes an upper limit on the sensitivity gain as the sensor's length is increased.

Although the invention has been described in detail in the foregoing for the purpose of illustration, it is to be understood that such detail is solely for that purpose and that variations can be made therein by those skilled in the art without departing from the spirit and scope of the invention as described by the following claims.

I claim:

1. A sensor for detecting species concentrations in an analyte comprising:
   an optical fiber used for detecting species concentrations in an analyte, said optical fiber having a core and an intermediate dielectric layer circumferentially surrounding the core, said core having an index of refraction greater than the index of refraction of the intermediate dielectric layer, said intermediate dielectric layer maintaining its integrity by not reacting with the analyte and enabling an evanescent wave to pass therethrough with minimal decay and being unreactive to light; and
   a modal selector disposed to launch light into the core of the optical fiber at a desired mode.

2. A sensor as described in claim 1 wherein the mode selector includes an optical source disposed to provide light to the core of the optical fiber;
   an aperture mask disposed between the core of the optical fiber and an optical source, said aperture mask determining the mode at which the light for the optical source is launched into the core of the optical fiber;
   a lens disposed between the aperture mask and the core of the optical fiber, said lens focusing light passing through the aperture mask into the core of the optical fiber; and
   a detector disposed to receive light emitted from the core of the optical fiber.

3. A sensor as described in claim 2 wherein the optical source is a collimated light source.

4. A sensor as described in claim 3 wherein said core is between 2 microns and 4 millimeters in diameter.

5. A sensor as described in claim 4 wherein the index of refraction of the core is between 1.3 and 4.

6. A sensor as described in claim 4 wherein the index of refraction of the intermediate dielectric layer is only less than the index of refraction of the core by some fraction $$\Delta = \frac{n_{core} - n_{inter}}{n_{core}}$$

where $n_{core}$ is the refraction index of the core and $n_{inter}$ is the index of refraction of the intermediate dielectric layer.

7. A sensor as described in claim 6 wherein the fraction $\Delta$ is $<0.01$.

8. A sensor as described in claim 7 wherein the intermediate dielectric layer is between 0.01 microns and 25 microns.

9. A sensor as described in claim 7 wherein the intermediate dielectric layer is a coating.

10. A sensor as described in claim 9 wherein the coating thickness is less than the wavelength of the light.

11. A sensor as described in claim 9 wherein the coating thickness is greater than the wavelength of the light.

* * * * *